(12) United States Patent
Brusilovsky et al.

(10) Patent No.: US 8,097,433 B2
(45) Date of Patent: Jan. 17, 2012

(54) DIAGNOSTIC COMPOSITION AND ARTICLE FOR MONITORING INTRAVAGINAL INFECTIONS

(75) Inventors: David Brusilovsky, Herzliya (IL); Hadar Kessary-Shoam, Zichron Yakov (IL); Menashe Terem, Yavne (IL)

(73) Assignee: Common Sense, Ltd., Caesarea (IL)

( * ) Notice: Subject to any disclaimer, the term of this patent is extended or adjusted under 35 U.S.C. 154(b) by 583 days.

(21) Appl. No.: 12/094,555

(22) PCT Filed: Nov. 22, 2005

(86) PCT No.: PCT/IL2005/001237
§ 371 (c)(1),
(2), (4) Date: Oct. 16, 2008

(87) PCT Pub. No.: WO2007/060649
PCT Pub. Date: May 31, 2007

(65) Prior Publication Data
US 2009/0275071 A1    Nov. 5, 2009

(51) Int. Cl.
*C12Q 1/02* (2006.01)
*A61F 13/15* (2006.01)
*A61F 6/06* (2006.01)
(52) U.S. Cl. .................... 435/29; 424/430; 604/358
(58) Field of Classification Search .............. None
See application file for complete search history.

(56) References Cited

U.S. PATENT DOCUMENTS

| | | | |
|---|---|---|---|
| 3,954,563 A | 5/1976 | Mennen | 195/197 |
| 4,532,216 A | 7/1985 | Wang | 436/2 |
| 5,214,821 A | 6/1993 | Burrow et al. | 15/210.1 |
| 5,217,444 A | 6/1993 | Schoenfeld | 604/361 |
| 5,660,790 A | 8/1997 | Lawrence et al. | 422/56 |
| 5,897,834 A | 4/1999 | Lawrence et al. | 422/56 |
| 5,910,447 A | 6/1999 | Lawrence et al. | 436/111 |
| 6,099,801 A | 8/2000 | Lawrence et al. | 422/56 |
| 6,627,394 B2 | 9/2003 | Kritzman et al. | 435/4 |
| 6,921,647 B2 * | 7/2005 | Kritzman et al. | 435/12 |
| 7,736,349 B2 * | 6/2010 | Gagliardi et al. | 604/385.23 |
| 2002/0041897 A1 | 4/2002 | Dang | 424/486 |
| 2003/0166293 A1 * | 9/2003 | Kritzman et al. | 436/111 |

FOREIGN PATENT DOCUMENTS
WO    WO 95/03423    2/1995

* cited by examiner

*Primary Examiner* — Vera Afremova
(74) *Attorney, Agent, or Firm* — Winston & Strawn LLP

(57) ABSTRACT

The present invention provides a non-toxic diagnostic composition for intravaginal monitoring of vaginal infections. The present invention further provides a diagnostic article for intravaginal monitoring of vaginal infections with the article including an absorbent material for absorbing vaginal secretions and a composition suitable for identification of the pH or the buffer capacities associated with vaginal secretions. The diagnostic composition provides a visible indication of vaginal infections, such as bacterial vaginosis.

6 Claims, No Drawings

DIAGNOSTIC COMPOSITION AND ARTICLE FOR MONITORING INTRAVAGINAL INFECTIONS

This application is a 371 filing of International Patent Application PCT/IL2005/001237 filed Nov. 22, 2005.

FIELD OF THE INVENTION

The present invention relates to the field of medical diagnostics and more specifically, to improved identification of vaginal infections such as bacterial vaginosis by using an intravaginal secretion-monitoring composition.

BACKGROUND OF THE INVENTION

Vaginal discharge caused by secretions from the vagina may occur throughout the menstrual cycle. Such discharge may result from both non-infectious causes and infectious causes. The non-infectious causes include physiological causes, such as puberty, menstrual cycle, sexual activity, pregnancy and menopause, as well as non-physiological causes such as the presence of a foreign body, chemical, drug, and gynecologic abnormalities. The infectious causes producing vaginal secretions include Candida albicans, Trichimonas vaginalis, and Bacterial vaginosis (BV).

Normal healthy vaginal tissue is populated by protective vaginal bacterial flora, such as hydrogen peroxide-producing lactobacilli. BV is an infection involving an imbalance in the vaginal bacterial flora. In this condition, the lactobacilli and other normal flora are replaced with pathogenic anaerobic coccobacilli. Studies associate BV with some serious conditions affecting the female reproductive system, encompassing complications of pregnancy, childbirth and fertility. These include pre-term birth, low birth weight infants, premature rupture of the membranes, chorionic and amnionic infection, infertility, ectopic pregnancy, and other perinatal/reproductive tract complications.

BV is one of the commonest causes of abnormal vaginal discharge. The condition is under diagnosed partly because of the lack of an easy and acceptable method of diagnosis. Genito-urinary medical physicians make the diagnosis of BV by various means including examining stained preparations of vaginal discharge under the microscope and relating this to the patient's symptoms. This is rarely performed by general practitioners, family planning doctors, gynecologists and other health care workers because of the lack of time and expertise.

An early study of BV involved comparisons of the pH of vaginal fluids of women known to be suffering from BV with those known to be free of the disease (Gardner et al., 1955, Am. J. Obstet. Gynecol. 69:962). All of the BV positive women in the study were determined to have a vaginal fluid pH greater than 4.5, and 91% of these women had a vaginal fluid pH greater than 5.0. Of the normal (disease-free) women in the test, 92% were found to have vaginal pH between 4.0 and 4.7. The conclusion drawn from the study was that a vaginal pH equal to or greater than 4.7 in conjunctions with other clinical criteria was indicative of the presence of BV.

BV can be diagnosed by external examinations of vaginal secretions, U.S. Pat. No. 4,532,216 discloses the use of quaternary ammonium polyelectrolyte salts in a test means, test device, and method for determining the ionic strength or specific gravity of a test sample as well as a method for making the device. U.S. Pat. No. 6,099,801 discloses a test device for detecting salts of volatile amines in aqueous fluids, useful in the diagnosis of bacterial vaginosis in vaginal secretions. U.S. Pat. Nos. 5,660,790 and 5,910,447 disclose a test device and a method for analyzing the pH of an aqueous liquid sample.

U.S. Pat. No. 5,897,834 discloses a device useful for the differentiation between urine and vaginal secretions associated with vaginosis or urine and amniotic fluid. The device includes the use of indicators with a negatively charged group immobilized to a solid polymer substrate containing quaternary ammonium groups. Further the device includes a gaseous amine-releasing reagent and an amine indicator. The use of the polymer substrate containing quaternary ammonium groups is disclosed to have an advantage of sharpening the pH dependent color transition. However, these test devices are not applicable for intravaginal examination.

BV can be also diagnosed by intravaginal secretion sampling. WO95/03423 discloses an amine tester for diagnosing bacterial vaginosis and vaginitis comprising at least one receptacle containing an alkaline medium; a test swab; and at least one control assembly for producing as a control smell volatilized amines, said test swab being, in use, contaminated with a sample from a vaginal discharge whereby a comparison of the smells resulting from the exposure of the test swab to the alkaline medium and from the control assembly enables the detection of volatilized amines from the test swabs.

U.S. Pat. No. 5,217,444 discloses a tampon for absorbing vaginal discharge, characterized in that the tampon includes two pH indicator materials of different pH values indicating by a color change the acidity or alkalinity of a liquid coming into contact with said materials, said pH indicator materials being included in the tampon so as to be wetted by the secretions absorbed by the tampon, thereby providing an indication of the health condition of the person's body. The specific compositions of the chemical means however are not defined.

U.S. Pat. Nos. 6,627,394 (the '394 patent) and 6,921,647 (the '647 patent) a continuation-in-part of the '394 patent, of the applicant of the present invention disclose a secretion-monitoring article for identifying a secreted biological fluid having a body with an absorbent material and least one pH determining member and a reagent associated with the absorbent material. The article is capable of indicating the presence of amniotic fluid, or secretions associated with bacterial, parasite, fungal, or yeast infections without giving a false positive result upon exposure to urine. However, the disclosed article may include unacceptable levels of cytotoxic components and thus is not suitable for use in intravaginal articles, such as a swab.

There is an unmet need for a non-toxic composition that can provide intravaginal monitoring of vaginal infections such as bacterial vaginosis.

SUMMARY OF THE INVENTION

The present invention overcomes the disadvantages of the prior art by providing a non-toxic composition that enables diagnosis of vaginal infections in an intravaginal sampling article, such as a swab. The invention further provides a non-toxic secretion-monitoring article comprising an absorbent material for absorbing vaginal secretions and a hydrophobic polymer composition comprising an indicator agent and an ion-balance reagent. The indicating composition is associated with the absorbent material such that the vaginal secretions absorbed by the absorbent material further contact the indicator composition so that a reliable indication of the pH as function of the buffer capacity of said secretions can be obtained.

The composition of the present invention is particularly useful in a clinical setting where the health care professional applies the vaginal secretion to the article and observes a fast color change within 1-10 seconds. Advantageously, said composition reacts with vaginal secretions containing protonated amine cations differently than with vaginal secretions that do not contain protonated amine cations.

According to one aspect, the present invention provides a diagnostic composition for intravaginal monitoring of vaginal infections comprising a pre-formed polymer in an amount that does not exceed about 45%; a plasticizer in an amount that does not exceed about 35%; a wetting agent in an amount that does not exceed about 40%; an ion-balance reagent in an amount that does not exceed about 5%; and an indicator agent in an amount that does not exceed about 2%; wherein the percents are weight percent based on the total dry weight of the composition and the total dry weight of the composition equals 100%.

According to current embodiments, the plasticizer is selected to be other than dibutylphthalate and the ion-balance reagent is selected to be other than methyl trioctyl-ammonium chloride since these components are considered to be cytotoxic.

According to one embodiment, the pre-formed polymer is in an amount of about 25% to 45%; the plasticizer is in an amount of about 18% to 35%; the wetting agent is in an amount of about 20% to 40%; the ion-balance reagent is in an amount of about 1% to 5%; and the indicator agent is in an amount of about 0.1% to 2%.

According to another embodiment, the pre-formed polymer is in an amount of about 30% to 40%; the plasticizer is in an amount of about 20% to 30%; the wetting agent is in an amount of about 30% to 37%; the ion-balance reagent is in an amount of about 1.5% to 3%; and the indicator agent is in an amount of about 0.3% to 1%.

According to one embodiment, the indicator agent is selected from the group consisting of nitrazine yellow, cresol red, alizarin, bromcresol purple, chlorophenol red, bromthymol blue, bromoxylenol blue, neutral red, phenol red, thymol blue, xylenol blue and m-cresol purple.

According to another embodiment, the ion-balance reagent is selected from the group consisting of tri-dodecylmethyl ammonium chloride, di(long-chain alkyl)dimethyl ammonium chloride, N-methyl-N,N-bis(long-chain alkanoyl oxyethyl)-N-(2-hydroxyethyl) ammonium methylsulfate, vinylbenzyl dimethylcocoammonium chloride, tricaprylylmethyl ammonium chloride, and cetyltimethyl ammonium chloride.

According to a further embodiment, the pre-formed polymer is selected from the group consisting of cellulose acetate, cellulose, sodium carboxymethyl cellulose, ethyl cellulose, and nitrocellulose.

According to still another embodiment, the wetting agent is selected from the group consisting of 2-ethoxy ethanol, triethylene glycol, ethylene glycol, and sorbitol.

According to still a further embodiment, the plasticizer is selected from the group consisting of dioctylphthalate, castor oil, diacetylated monoglycerides, diethyl phthalate, glycerin, mono- and di-acetylated monoglycerides, polyethylene glycol, propylene glycol, triacetin, triethyl citrate, bis-(2-butoxyethyl) adipate, and bis-(2-ethylhexyl) sebacate.

According to a currently preferred embodiment, the pre-formed polymer is cellulose acetate; the plasticizer is dioctylphthalate; the wetting agent is ethoxy ethanol; the ion-balance reagent is a tri-dodecylmethyl ammonium chloride; and the indicator agent is nitrazine yellow.

According to one embodiment, the diagnostic composition, further comprising a solvent. According to another embodiment, the solvent is acetone.

According to one embodiment, the vaginal infection is bacterial vaginosis. According to another embodiment, said diagnostic composition changes color, which is stable for about two hours when contacted by a vaginal secretion associated with bacterial vaginosis.

According to a further embodiment, said composition changes color within 1-10 seconds when contacted by a vaginal secretion associated with bacterial vaginosis.

According to another aspect, the present invention provides a diagnostic article for intravaginal monitoring of vaginal infections that comprises the diagnostic composition of the invention and a body that serves as a support surface for the diagnostic composition. According to one embodiment, the diagnostic article comprising a body and an absorbent material for absorbing vaginal secretions, the material comprising a diagnostic composition comprising a pre-formed polymer in an amount that does not exceed about 45%; a plasticizer in an amount that does not exceed about 35%; a wetting agent in an amount that does not exceed about 40%; an ion-balance reagent in an amount that does not exceed about 5%; and an indicator agent in an amount that does not exceed about 2%; wherein the percents are weight percent based on the total dry weight of the composition and the total dry weight of the composition equals 100%.

According to current embodiments, the plasticizer is selected to be other than dibutylphthalate and the ion-balance reagent is selected to be other than methyl trioctyl-ammonium chloride since these components are considered to be cytotoxic.

According to one embodiment, the pre-formed polymer is in an amount of about 25% to 45%; the plasticizer is in an amount of about 18% to 35%; the wetting agent is in an amount of about 20% to 40%; the ion-balance reagent is in an amount of about 1% to 5%; and the indicator agent is in an amount of about 0.1% to 2%.

According to a currently preferred embodiment, the diagnostic article is a swab, the tip of which is coated with absorbent material. According to one embodiment, the absorbent material is polyester. According to a currently preferred embodiment, the polyester is knitted polyester or woven polyester.

According to a further aspect, the present invention provides a method of diagnosing vaginal infections comprising the steps of:
  (i) providing a diagnostic nontoxic swab according to the invention;
  (ii) contacting vaginal secretion intravaginally; and
  (iii) visually interpreting the color changes which indicate the pH and/or buffer capacity of the vaginal secretions correlates with vaginal infection.

DETAILED DESCRIPTION OF THE INVENTION

The present invention provides a non-toxic diagnostic composition for intravaginal monitoring of vaginal infections. The present invention further provides a diagnostic article for intravaginal monitoring of vaginal infections comprising an absorbent material for absorbing vaginal secretions comprising a composition suitable for identification of the pH associated with vaginal secretions. The diagnostic composition provides a visible indication of vaginal infections, such as bacterial vaginosis.

The secretion-monitoring intravaginal article of the present invention is accurate, reliable, efficient, not toxic and easy to use. The article is selected from the group consisting of a swab, intravaginal tampon, tampon-like device, and intravaginal sponge. The article may be formed from a variety of different absorbent materials, such as polyester, polypropylene, paper, cotton, rayon, pulp, etc., and may possess any desired shape and/or size.

The composition is applied to the swab for example by dipping the swab in the composition or by spraying or spreading the composition onto the swab. The swab with the applied composition is allowed to dry. When dry, the indicator is bound to the substrate with the help of the polymer.

The secretion-monitoring swab of the present invention is used for the identification of vaginal infections such as bacterial vaginosis (BV) or parasite. Bacterial vaginosis (BV) is characterized by production of increased quantities of malodorous vaginal discharge. The vaginal discharge of women with BV is described as being thin (low viscosity), off-white-gray (milk-like consistency), and homogeneous (distinctly not curd-like).

In the vagina there are no glands so that the fluid which it contain results from cervical secretion, vulvar secretions from sebaceous, sweat, Bartholine and Skeens glands, exfoliated cells, endometrial and oviductal fluids but mainly from liquid transudation through the vaginal epithelial walls.

As mentioned above, one of the characteristics of BV is the homogeneous discharge. A women having BV typically has an increase in the discharge amount. The source of this liquid is extracellular fluid (interstitial fluid) that surrounds the epithelial cells in the vagina wall.

The ionic composition of the extracellular fluid and the plasma is quite similar with some differences reflecting the inability of large solutes, like proteins, to cross the cells wall.

A decrease in protein levels and other large organic molecules and the increase of water content in BV secretions lowers the buffering capacity of the secretions. Thus, secretions associated with BV have a lower buffer capacity than healthy vaginal secretions.

The term "substantially different pH ranges" is to be construed in its most general sense and refers to any pH ranges that do not span exactly the same range. Namely, pH ranges having different upper limits and/or different lower limits are substantially different. These different pH ranges may comprise overlapping pH values, such as a pH range of 5.0-8.0 and a pH range of 4.0-7.0 and may be also essentially different, namely, devoid of any overlapping pH values.

When used in a medical setting, it is imperative that there be substantially no leaching of indicator components from the substrate to which the indicator composition is attached. The attachment of indicators to a substrate is well within the ability of one skilled in the art. One family of chemical compounds that are suitable for use as the indicators of the present invention without leaching are indicators with negative functional groups. Suitable indicators include nitrazine yellow, thymol blue, bromthymol blue, xylenol blue, bromoxylenol blue, phenol red, m-cresol purple, chlorophenol red, bromocresol purple, alizarin, neutral red, and cresol red. A list of other suitable indicators can be found, for example, in U.S. Pat. No. 5,897,834, incorporated herein by reference. It is clear to one skilled in the art that the indicators specifically mentioned herein are just examples and any suitable indicators may be used.

According to a currently preferred embodiment of the present invention, an indicator composition is made with nitrazine yellow that indicates the presence of a fluid with a pH of around 4.2 to 7.0. Upon contacting vaginal secretions having a pH of 5.2 or greater, the color changes from pale yellow to blue or green, which indicates possible BV or Trichomonas. At pH of 5.1 or lower, but greater than 4.2, the color change depends on the ionic strength of the vaginal discharge: the more fluidic is the discharge; the change in color is less evident. Fluids with pH levels of 4.2 or lower do not cause a change in the color of the indicating composition.

According to one embodiment of the present invention, a polymer solution is prepared containing a preformed polymer. The preformed polymer can be selected from various preformed polymers such as cellulose, sodium carboxymethyl cellulose, ethyl cellulose, and nitrocellulose, although cellulose acetate is currently preferred.

According to another embodiment of the present invention, a plasticizer other than dibutylphthalate can be selected from various plasticizer such as castor oil, diacetylated monoglycerides, diethyl phthalate, glycerin, mono- and di-acetylated monoglycerides, polyethylene glycol, propylene glycol, triacetin, triethyl citrate, bis-(2-butoxyethyl) adipate, and bis-(2-ethylhexyl) sebacate, although dioctylphthalate is currently preferred.

According to a further embodiment of the present invention, an ion-balance reagent other than methyl trioctyl-ammonium chloride can be selected from various ion-balance reagents such as di(long-chain alkyl)dimethyl ammonium chloride, N-methyl-N,N-bis(long-chain alkanoyl oxyethyl)-N-(2-hydroxyethyl) ammonium methylsulfate, vinylbenzyl dimethylcocoammonium chloride, tricaprylylmethyl ammonium chloride, and cetyltimethyl ammonium chloride, although tri-dodecylmethyl ammonium chloride is currently preferred.

According to still another embodiment of the present invention, a wetting agent can be selected from various wetting agents such as triethylene glycol, ethylene glycol, and sorbitol, although 2-ethoxy ethanol is currently preferred.

The present invention provides a secretion-monitoring article comprising a body and an absorbent material for absorbing vaginal secretions comprising a hydrophobic polymer composition comprising cellulose acetate in an amount that about 45%; dioctylphthalate in an amount that does not exceed about 35%; 2-ethoxy ethanol in an amount that does not exceed about 40%; tridodecylmethyl ammonium chloride in an amount that does not exceed about 5%; and nitrazine yellow in an amount that does not exceed about 2%; wherein the percents are weight percent based on the total dry weight of the composition and the total dry weight of the composition equals 100% and the composition provides an indication of physiological conditions associated with the pH or the buffer capacities of the vaginal secretions.

According to one embodiment, the cellulose acetate is in an amount of about 25% to 45%; the dioctylphthalate is in an amount of about 18% to 35%; the 2-ethoxy ethanol is in an amount of about 20% to 40%; the tridodecylmethyl ammonium chloride is in an amount of about 1% to 5%; and the nitrazine yellow is in an amount of about 0.1% to 2%.

The present invention further provides a method of diagnosing vaginal infections comprising the steps of:
 (i) providing a diagnostic nontoxic swab according to the invention;
 (ii) inserting into the vagina the diagnostic swab;
 (iii) contacting vaginal secretion;
 (iv) removing said swab from the vagina; and
 (v) visually interpreting the color changes which indicate the pH and/or buffer capacity of said vaginal secretions correlates with vaginal infection.

Having now generally described the invention, the same will be more readily understood through reference to the following examples, which are provided by way of illustration and are not intended to be limiting of the present invention.

EXAMPLES

Example 1

Cytotoxicity Study Using the ISO Agarose Overlay Method

An in vitro biocompatibility study, based on the requirements of the International Organization for Standardization (ISO 10993-5) and USP <87>, was conducted using the indicating composition disclosed in Table 1 in order to determine its cytotoxicity.

TABLE 1

Components of the indicating composition

| Material | Function | % W/W |
|---|---|---|
| Acetone | Solvent | 0.00 |
| Cellulose Acetate | Polymer | 35.39 |
| Dibutylphthalate | Plasticizer | 26.37 |
| Aliquat 336 (methyl trioctyl-ammonium chloride), $[N^+CH_3(C_8H_{17})_3]Cl^-$ | Ion-balance reagent | 4.77 |
| 2-Ethoxy ethanol | Wetting agent | 32.91 |
| Nitrazine Yellow | An indicator substance | 0.57 |

A 1 cm×1 cm sample of coated polyester swab tips with the indicating composition, a negative control (high density polyethylene), and a positive control (latex) were each placed on triplicate agarose surfaces, directly overlaying confluent monolayers of L-929 mouse fibroblast cells.

After incubating at 37° C. in 5% $CO_2$ for 24 hours, the cell culture was colored by neutral red and examined macroscopically for cell decolorization around the test article and controls to determine the zone of cell lysis. The cultures were then examined microscopically (100×, light microscope) to verify any decolorized zones and to determine cell morphology in proximity to the articles.

Under the conditions of this study, the indicating composition showed evidence of causing severe cell lysis and toxicity. The indicating composition did not meet the requirements of the USP <87> since the grade was greater than a grade 2 (mild reactivity). The negative control and the positive control performed as anticipated.

Example 2

New Non-Cytotoxic Formulation of the Indicating Composition

Since the indicating composition disclosed in Table 1 showed an unexpectedly high level of cytotoxicity, the most toxic components (dibutylphthalate; plasticizer and methyl trioctyl-ammonium chloride; ion-balance reagent) were changed, in order to minimize the cytotoxicity level. Dioctylphthalate and tri-dodecylmethyl ammonium chloride (TDMACl) were chosen and their concentrations optimized to achieve the optimal pH dynamic range. The new formulation of the indicating composition comprising cellulose acetate in an amount of 26.94%; dioctylphthalate in an amount of 18.86%; 2-ethoxy ethanol in an amount of 25.05%; tridodecylmethyl ammonium chloride in an amount of 1.79%; nitrazine yellow in an amount of 0.43%; wherein the percents are weight percent based on the total weight of the mixture and the total weight of the mixture equals 100% (Table 2).

TABLE 2

Components of the new indicating composition

| Chemical | % W/W | Function |
|---|---|---|
| Acetone | 0.00 | Solvent |
| Cellulose Acetate | 36.87 | Polymer |
| Dioctylphthalate | 25.81 | Plasticizer |
| TDMACl | 2.45 | Ion-balance reagent |
| 2-Ethoxy Ethanol | 34.29 | Wetting agent |
| Nitrazine Yellow | 0.59 | Indicator |

Example 3

Cytotoxicity Study Conducted on the New Indicating Composition

An in vitro biocompatibility study as described in EXAMPLE 1 was conducted on the new indicating composition in order to determine its cytotoxicity. Under the conditions of this study, the indicating composition showed no evidence of causing severe cell lysis or toxicity. The new indicating composition met the requirements of the USP <87> since the grade was less than a grade 2 (mild reactivity). The negative control and the positive control performed as anticipated. Thus the new indicating composition maybe advantageously used for detecting intravaginal infections.

Example 4

Method for Preparation of Non-Toxic Secretion-Monitoring Swab (Table 3)

The method for preparation of non-toxic secretion-monitoring swab comprising the steps of:

Step 1: To a 90 ml of Acetone add 900 mg Cellulose acetate, 640 µl Dioctylphthalate, 60 mg TDMACl, 900 µl 2-Ethoxy ethanol and 14.4 mg nitrazine yellow dissolved in 900 µl DDW.

Step 2: Stir the mixture for few minutes to complete dissolving.

Step 3: Coat a tip of a swab with the polymer solution to give the desired product.

Step 4: Dry over night.

The tip may be prepared by using a short strip, rolled on the stick of the swab, or by coating the tip of an integrated swab, where the tip consists of any screening fabric.

TABLE 3

Components for the preparation of the non-toxic secretion-monitoring swab

| Chemical | Quantity | % W/W | Function |
|---|---|---|---|
| Acetone (ml) | 90 | 95.52 | Solvent |
| Cellulose Acetate (g) | 0.9 | 1.21 | Polymer |
| Dioctylphthalate (ml) | 0.64 | 0.85 | Plasticizer |
| TDMACl (g) | 0.06 | 0.08 | Ion-balance reagent polymer |
| 2-Ethoxy Ethanol (ml) | 0.9 | 1.12 | Wetting agent |
| Nitrazine Yellow (g) | 0.0144 | 0.02 | Indicator |
| DDW (ml) | 0.9 | 1.21 | Co-solvent (used for dissolving the Nitrazine Yellow) |

Example 5

Stability of Indication Provided by the Composition of the Invention

The stability of indication provided by the composition of the invention (Table 2) was compared with the stability of the composition disclosed in Table 1. The visual indication of the composition of the invention was stable for about two hours (Table 4).

TABLE 4

Stability of Indication

| Time | New Indicator composition | Previous Indicator composition |
| --- | --- | --- |
| 0 | original | original |
| 5 minutes | colored | colored |
| 1 hour | colored | colored |
| 2 hours | colored | colored |
| 24 hours | back to original color | colored |

Example 6

Reducing the Amount of time Required for Obtaining Reliable Results

The composition disclosed in Table 1 takes up to 20 minutes for the color change to occur. In the clinic the practitioners need a much faster tool. The composition of the present invention takes only 2-5 seconds for the color change to occur.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It should be understood that the detailed description and specific examples, while indicating preferred embodiments of the invention, are given by way of illustration only, since various changes and modifications within the spirit and scope of the invention will become apparent to those skilled in the art from this detailed description.

The invention claimed is:

1. A diagnostic article for intravaginal monitoring of vaginal infections including bacterial vaginosis comprising a body and an absorbent material for absorbing vaginal secretions, the material comprising a diagnostic composition comprising a pre-formed polymer; a plasticizer; a wetting agent; an ion-balance reagent; and an indicator agent; wherein the pre-formed polymer is cellulose acetate and is present in an amount of about 30% to 40%; the plasticizer is dioctylphthalate present in an amount of about 20% to 30%; the wetting agent is ethoxy ethanol and is present in an amount of about 30% to 37%; the ion-balance reagent is a tridodecylmethyl ammonium chloride and is present in an amount of about 1.5% to 3%; and the indicator agent is nitrazine yellow and is present in an amount of about 0.3% to 1%; wherein the percents are weight percent based on the total dry weight of the composition and the total dry weight of the composition equals 100%.

2. The diagnostic article of claim 1, further comprising a solvent.

3. The diagnostic article of claim 1, wherein the composition changes color, when contacted by a vaginal secretion associated with bacterial vaginosis, with the color change occurring within 1-10 seconds and being stable for about 1 hour.

4. The diagnostic article of claim 1, wherein the article is a polyester swab.

5. A method of diagnosing vaginal infections which comprises:
    contacting vaginal secretion intravaginally with the diagnostic article according to claim 1; and
    visually interpreting the color changes which indicate the pH or buffer capacity of the vaginal secretions to correlate with a vaginal infection.

6. The method of claim 5, wherein the composition changes color when contacted by a vaginal secretion associated with bacterial vaginosis, with the color change occurring within 1-10 seconds and being stable for about 1 hour.

* * * * *